US012594298B2

(12) United States Patent
Dennett et al.

(10) Patent No.: US 12,594,298 B2
(45) **Date of Patent: \*Apr. 7, 2026**

(54) METHODS OF ADMINISTERING SAFE COLON CLEANSING COMPOSITIONS

(71) Applicant: Azurity Pharmaceuticals, Inc., Woburn, MA (US)

(72) Inventors: Edmund V. Dennett, Walpole, MA (US); Mark Cleveland, Norwell, MA (US); Russell W. Pelham, Duxbury, MA (US); Matthew Walker, Brighton, MA (US)

(73) Assignee: Azurity Pharmaceuticals, Inc., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/172,077

(22) Filed: Apr. 7, 2025

(65) Prior Publication Data

US 2025/0228888 A1     Jul. 17, 2025

Related U.S. Application Data

(63) Continuation of application No. 18/792,849, filed on Aug. 2, 2024, now Pat. No. 12,290,529, which is a continuation of application No. 18/743,526, filed on Jun. 14, 2024, now Pat. No. 12,239,659.

(60) Provisional application No. 63/521,314, filed on Jun. 15, 2023.

(51) Int. Cl.
| | |
|---|---|
| *A61K 31/765* | (2006.01) |
| *A61K 9/08* | (2006.01) |
| *A61K 33/04* | (2006.01) |
| *A61K 47/02* | (2006.01) |
| *A61K 47/26* | (2006.01) |
| *A61P 1/10* | (2006.01) |

(52) U.S. Cl.
CPC .............. *A61K 31/765* (2013.01); *A61K 9/08* (2013.01); *A61K 33/04* (2013.01); *A61K 47/02* (2013.01); *A61K 47/26* (2013.01); *A61P 1/10* (2018.01)

(58) Field of Classification Search
CPC ........ A61K 31/765; A61K 9/08; A61K 33/04; A61K 47/02; A61P 1/10
See application file for complete search history.

(56) References Cited

U.S. PATENT DOCUMENTS

| | | | |
|---|---|---|---|
| 3,873,694 | A | 3/1975 | Kanig |
| 4,975,286 | A | 12/1990 | Hechter |
| 5,124,144 | A | 6/1992 | Giorgetti et al. |
| 5,616,346 | A | 4/1997 | Aronchick |
| 6,162,464 | A | 12/2000 | Jacob et al. |
| 6,235,745 | B1 | 5/2001 | Megens |
| 6,946,149 | B2 | 9/2005 | Cleveland |
| 7,169,381 | B2 | 1/2007 | Barras et al. |
| 7,332,184 | B2 | 2/2008 | Vanner et al. |
| 7,658,914 | B2 | 2/2010 | Barras et al. |
| 7,687,075 | B2 | 3/2010 | Skiendzielewski et al. |
| 7,998,510 | B2 | 8/2011 | Caswell |
| 8,425,944 | B2 | 4/2013 | Caswell |
| 8,507,009 | B2 | 8/2013 | Skiendzielewski et al. |
| 8,778,306 | B2 | 7/2014 | Balwich |
| 9,238,075 | B2 | 1/2016 | Gorelick et al. |
| 9,433,660 | B2 | 9/2016 | Gorelick et al. |
| 9,919,007 | B2 | 3/2018 | Dennett, Jr. et al. |
| 2005/0271749 | A1 | 12/2005 | Borody et al. |
| 2009/0258090 | A1 | 10/2009 | Cleveland |
| 2012/0265011 | A1 | 10/2012 | Pelham |
| 2013/0189377 | A1 | 7/2013 | Cockett et al. |
| 2014/0087007 | A1 | 3/2014 | Cleveland et al. |
| 2020/0352855 | A1 | 11/2020 | Cleveland et al. |

FOREIGN PATENT DOCUMENTS

| | | |
|---|---|---|
| CN | 101087593 | 12/2007 |
| WO | 03092589 | 11/2003 |
| WO | 2009108730 | 9/2009 |
| WO | 2012013928 | 2/2012 |
| WO | 2013059881 | 5/2013 |
| WO | 2014044407 A8 | 9/2014 |
| WO | 2014144407 | 9/2014 |

OTHER PUBLICATIONS

Hamed Laroui et al. Dextran Sodium Sulfates (DSS) Induces Colitis in Mice by forming Nano-Lipocomplexes with Medium-Chain-Length Fatty Acids in the Colon PLoS One, 7(3):e32084 (2012).
Russel W. Pelham, et al. Safety of Oral Sulfates in Rats and Dogs Contrasted with Phosphates-Induced Nephropathy in Rats. International J of Toxicology 28(2):99-112 (2009).
Chavous, 2013, Chart, Description—CN10187593 & U.S. Pat. No. 3,873,694.
Sodium Sulphate, Potassium Sulfate and Magnesium Sulfate Oral Solutions; PEG-3350, Sodium Chloride, Sodium Bicarbonate and Potassium Chloride for Oral Solution (SUCLEAR), National Drug Monograph, Nov. 2004.
Chavous 2013, Chart, Descriptio—WO03/092589 and U.S. Pat. No. 3,873,694.
Fleet Corporation, Fleet PhosphoSoda Label, 1999.
Robert H. Hawes. A consensus document on Bowel Preparation Before Colonoscopy: Prepared by a Task Force From the American Society of Colon and Rectal Surgeons (ASCRS), the American Society for Gastrointestinal Endoscopy (ASGE), and the Society of American Gastrointestinal and Endoscopic Surgeons (SAGES). Gastrointestinal Endoscopy 63(7):894-909 (2006).
European Search Report EP15840422..8, Apr. 4, 2018.
Braintree Laboratories, SUPREP, Aug. 2010.

*Primary Examiner* — Zohreh A Fay
(74) *Attorney, Agent, or Firm* — McNeill PLLC

(57) ABSTRACT

Disclosed herein are methods of administering compositions comprising a mixture of salts that induce purgation of the colon and are useful to cleanse the colon. Furthermore, the disclosed methods prevent degradation of PEG and allow for cleansing of the colon without the use of adjunct laxatives, including stimulant laxatives such as bisacodyl. The disclosed methods are superior to the prior art in that they allow for higher tolerability, improved safety, lower volumes, and improved patient compliance.

3 Claims, No Drawings

1

METHODS OF ADMINISTERING SAFE COLON CLEANSING COMPOSITIONS

FIELD

This disclosure relates generally to the field of medicine and particularly to gastrointestinal diagnostic and surgical procedures.

BACKGROUND

When performing medical or diagnostic procedures on the colon, the colon must be cleansed of fecal matter to permit adequate visualization of the intestinal mucosa. This is important prior to, for example, diagnostic procedures such as flexible sigmoidoscopy or colonoscopy, diagnostic examinations widely performed to screen patients for diseases of the colon. In addition, it is important that the intestines be cleansed thoroughly in order to obtain satisfactory radiographs of the colon.

Existing bowel preparations are generally presented in a liquid form, such as the isotonic large volume preparations GoLYTELY and NuLYTELY which are based on polyethylene glycol (PEG) as the osmotic agent, or the smaller volume preparations such as MOVIPREP (a slightly hypertonic solution also based on PEG), SUPREP (based on sulfate as the osmotic agent) and Phosphosoda (based on phosphate). The larger volume preparations require ingestion of up to 4 liters (about 1 gallon) of solution (Davis et al. 1980; Fordtran et al. 1990). While recognized as the safest products, these large-volume preparations produce patient discomfort often resulting in poor compliance due to the large volume of salty tasting solution that must be consumed. An early innovation attempting to solve this problem was the development of a split dose hypertonic solution. The product, sold under the name Phosphosoda, was recognized to produce excellent bowel cleansing and required the ingestion of only a small volume of solution (Vanner et al. 1990). The product was also made into tablets, sold under the name Osmoprep (Aronchick et al. 2000). Although these products enjoyed improved patient tolerance, because they were formulated using salts of phosphate, they became associated with risk of renal failure due to renal calcium phosphate deposition (resulting from absorption of the phosphate anion) eventually prompting the FDA to issue a warning concerning their use (USFDA Alert 2008).

To address concerns regarding compliance and safety, medical practitioners developed a bowel prep comprising a combination of MiraLax® (a PEG based over the counter laxative) in combination with sports drinks such as Gatorade® and stimulant laxatives such as bisacodyl (see e.g., my dot clevelandclinic.org/-/ . . . /colonoscopy-prep/colonoscopy-prep-miralax.ashx). This combination addresses taste concerns but requires stimulant laxatives to provide a sufficient bowel cleansing.

The administration protocol involves taking bisacodyl the evening before the procedure and a couple hours after taking the bisacodyl, taking a mixture of MiraLax® and Gatorade® (PEG-SD) in 8-ounce volumes every 15 minutes until the solution has been completely consumed (id.). This procedure has several drawbacks, including lack of patient compliance due to bloating, cramps, poorly formulated electrolyte replenishment, a large amount of fermentable sugars and other potential physiologic and gastrointestinal issues, as well as depending on the patient to perform properly the process of mixing the MiraLax®/Gatorade® solution, and depending on the patient to take the bisacodyl at the proper time prior to consuming the MiraLax®/Gatorade® solution and hyponatremia has been observed with the preparation (*J Clin Gastroenterol* 2006; 40: 558-9). The procedure is also "off-label" and has not been approved by the FDA for use. In addition, the preparations use stimulant laxatives such as bisacodyl, which should not be administered in doses of greater than 20 mg.

SUMMARY

As disclosed herein, the inventors have discovered a method of administering a composition of PEG and sulfate that yields substantial stool output and cleanses the colon while maintaining a satisfactory patient safety profile. The inventors further surprisingly discovered that the composition has a good taste and can replace the need for Gatorade® to be included in the preparation. The inventors further surprisingly discovered that a PEG-based product could be provided with a flavoring agent comprising acidic components such that the PEG was not degraded to yield byproducts. Furthermore, the method of administration of the composition allows for a substantial elimination of the need for an adjunct laxative such as stimulant laxatives including bisacodyl. Furthermore, another aspect of the disclosed compositions allows for better taste and reduction in gas production caused by fermentation of fermentable sugars. In certain aspects, the compositions utilize non-fermentable sugars.

The inventors have developed a composition that comprises PEG, such as PEG-350 in combination with sodium sulfate, magnesium sulfate, potassium chloride, and sodium chloride. Unlike Miralax®, the inventors utilize the sulfate anion to induce additional cleansing of stool along with PEG. Also, the inventors include the chloride anion as well as the potassium, sodium, and magnesium cations to balance the electrolytes. These cations and anions avoid issues relating to electrolyte loss, absorption, and anion gap.

These issues have become concerns regarding the safety and efficacy of Miralax®, leading to caution regarding its use (Matro et al, 2014; Schoenfeld, 2013). For example, Matro et al (2014) randomized patients to receive PEG-SD (N=180) or PEG-EA (N=184), which is an approved bowel preparation (MOVIPREP®) and they had clinical chemistry data at baseline and on the day of colonoscopy. Although the incidence of hyponatremia (serum sodium<135 mmol/L) was higher in the osmotically unbalanced PEG-SD group, (3.9%) vs the PEG-EA treated group (2.2%), it did not differ statistically. For other electrolytes, small but statistically significant changes from baseline to colonoscopy occurred with PEG-SD for sodium, potassium and chloride (P=0.001, 0.012, 0.001, respectively). PEG-SD has also been associated with the development of hyponatremia, leading to the hospitalization of eight and serious sequelae in two of patients (Lewis and Schoenfeld, 2011).

Regarding the efficacy of PEG-SD, studies have concluded that PEG-SD is inferior in the rate of preparations considered "excellent" by the endoscopist (Matro et al. 2014). Patients consuming the PEG-SD also drink additional fluids and are usually instructed to receive a de-bulking laxative such as OTC bisacodyl prior to the PEG-SD consumption. Bisacodyl is a poorly absorbed stimulant laxative, which has been in use since 1953. Bisacodyl acts to stimulate peristalsis in the colon resulting in stool evacuation and is classified as a Category I OTC laxative. There have been reports of ischemic colitis in patients with use of 10 mg bisacodyl as part of a now-discontinued bowel preparation (Food and Drug Administration Docket No. FDA-2010-P-

0507). Furthermore, an additional concern is that PEG-SD contains carbohydrates and sugars, leading to the possibility of the formation of volatile end products which could provide a hazard doting electrocautery.

Recognizing these issues, the inventors developed a method of administering a composition that eliminated the poor taste of sulfate cations and PEG, while eliminating the need for adjunct laxatives. The methods disclosed herein address issues relating to the use of a composition effective to cleanse the colon without the need for adjunct laxatives and to eliminate compliance issues relating to the poor taste of PEG and sulfate salts. The compositions (alternatively, "formulations") are effective and safe to cleanse the colon of a subject. The compositions are effective to induce purgation of the colon and are further safe and effective to cleanse the colon. As used herein, the term "purgation" means evacuation of a copious amount of stool from the bowels after oral administration of a composition. Furthermore, disclosed herein are methods for cleansing of the colon of a subject, as well as methods for purging the colon of a subject. As used herein, "purging" means evacuating a copious amount of stool from the bowels after oral administration of a composition. The disclosed compositions also do not cause clinically significant electrolyte shifts and are thus useful for preparation of patients for diagnostic and surgical proce-dures. Such diagnostic and surgical procedures include, but are not limited to, colonoscopy, sigmoidoscopy, radio-graphic examination, bowel surgery, colon resection, and other colorectal procedures. Furthermore, the present com-positions, compositions, and methods allow for treatment of conditions such as fecal retention, constipation, and hard stools by providing a composition that can be used as a laxative when administered in lower doses than used for colon cleansing.

Aspects of the methods disclosed herein include provid-ing a first container of a first portion of a first dose of a colon cleansing product comprising about 170 to about 180 grams of polyethylene glycol, about 5.0 to about 8.0 grams of sodium sulfate, about 0.5 to 3.0 grams of potassium chlo-ride, about 0.4 to about 1.5 grams of magnesium sulfate, about 0.4 to about 1.4 grams of sodium chloride, about 0.40 grams to about 0.45 grams of lemon-lime flavor, about 0.55 grams to about 0.65 grams of sucralose, about 0.03 grams to about 0.05 grams of neotame, and about 0.008 grams to about 0.015 grams of advantame. Aspects further include providing a second container of a second portion of the first dose of a colon cleansing product comprising from about 1.35 grams to about 1.60 grams of malic acid and from about 1.600 grams to about 1.70 grams of citric acid. The method further includes mixing the first container and second con-tainer together to form a first mixture and then mixing the first mixture with about 0.5 liters to about 1.0 liters of water to form a first liquid colon cleansing dose. The method further comprises consuming the first liquid colon cleansing dose. The method further comprises providing a third con-tainer of a first portion of a second dose of a colon cleansing product comprising about 170 to about 180 grams of poly-ethylene glycol, about 5.0 to about 8.0 grams of sodium sulfate, about 0.5 to 3.0 grams of potassium chloride, about 0.4 to about 1.4 grams of sodium chloride, about 0.4 to about 1.5 grams of magnesium sulfate, about 0.40 grams to about 0.45 grams of lemon-lime flavor, about 0.55 grams to about 0.65 grams of sucralose, about 0.03 grams to about 0.05 grams of neotame, and about 0.008 grams to about 0.015 grams of advantame. Aspects further include providing a fourth container of a second portion of the second dose of a colon cleansing product comprising from about 1.35 grams to about 1.60 grams of malic acid and from about 1.600 grams to about 1.70 grams of citric acid. The method further includes mixing the third container and fourth container together to form a second mixture and then mixing the second mixture with about 0.5 liters to about 1.0 liters of water to form a second liquid colon cleansing dose. The method further comprises consuming the second liquid colon cleansing dose. In some embodiments, the method involves consuming the first liquid colon cleansing dose in 150 ml to 300 ml volumes every 15 minutes. In other embodiments, the method involves consuming the second liquid colon cleansing dose in 150 ml to 300 ml volumes every 15 minutes. In particular embodiments, the method comprises administering the second liquid colon cleansing dose at least 4 hours and no longer than 24 hours after the first liquid colon cleansing dose. In further embodiments, the methods can be performed by supplying a patient with first, second, third, and fourth containers that are each liquid volumes. In such embodiments, the methods do not require forming the first and second mixtures and then mixing those mixtures with water. As used herein, the term "a" means one or more unless specifically defined otherwise. In certain embodiments, the disclosed compositions comprise sulfate salts.

Aspects of disclosed herein include compositions for cleansing the colon of a subject (e.g., patient). The compo-sitions comprise from about 325.00 grams to about 375.00 grams of polyethylene glycol, from about 10.00 grams to about 25.00 grams of sodium sulfate, about 1.00 grams to about 2.50 grams of magnesium sulfate, from about 1.00 grams to about 3.00 grams of potassium chloride and from about 1.00 grams to about 3.00 grams of sodium chloride. The compositions further comprise a flavoring agent com-prising a flavor in combination with one or more sweeteners.

In some embodiments, the disclosed compositions com-prise sodium sulfate. In other embodiments, the total dose of composition comprises from about 10.0 grams to about 25.0 grams of sodium sulfate. In specific embodiments, the total dose of composition comprises from about 15.0 grams to about 20.0 grams of sodium sulfate. In more specific embodiments, the total dose of composition comprises about 17.0 grams of sodium sulfate. As used herein, the term "about" means within +/−10% of the recited value. For instance, about 2.0 would cover from 1.8 to 2.2.

In some embodiments, the composition further comprises malic acid and citric acid. In other embodiments, the com-position comprises from about 1.35 grams to about 1.60 grams of malic acid. In particular embodiments, the com-position comprises from about 1.600 grams to about 1.70 grams of citric acid.

In still other embodiments, the composition further com-prises a flavoring agent. In more embodiments, the flavoring agent comprises a flavor and a combination of sweeteners. In particular embodiments, the sweeteners comprise non-fermentable carbohydrates. In yet more embodiments, the combination of sweeteners comprises less than about 10%, 5%, 1%, or 0.5% fermentable carbohydrates. In some embodiments, the composition comprises less than about 0.01% fermentable carbohydrates. In yet more embodi-ments, the combination of sweeteners comprises sucralose, neotame, and advantame. In particular embodiments, the composition comprises about 0.003% of advantame. In still more embodiments, the composition comprises from about 0.400 grams to about 0.500 grams of the flavor. In even more embodiments, the composition comprises from about 0.400 grams to about 0.800 grams of sucralose. In further embodi-ments, the composition comprises from about 0.020 grams to about 0.050 grams of neotame. In still further embodiments, the composition comprises sodium from about 0.005 grams to about 0.020 grams of advantame. In even further embodiments, the composition further comprises a liquid.

In some embodiments, the liquid is water. In other embodiments, the composition further comprises lemon-lime flavor, sucralose, neotame, advantame, malic acid, and citric acid.

In certain embodiments, the composition comprises about 357.40 grams of polyethylene glycol, about 17.00 grams of sodium sulfate, about 1.800 grams of magnesium sulfate, about 2.240 grams of potassium chloride, about 2.00 grams of sodium chloride, about 0.410 grams of lemon-lime flavor, about 0.600 grams of sucralose, about 0.038 grams of neotame, and about 0.012 grams of advantame.

In more embodiments, the composition is reconstituted to 1.0 L or 2.0 L of water. In particular embodiments, the composition comprises from about 0.5 L to about 2.0 L of water. In more particular embodiments, the composition comprises about 0.846 L or about 1.692 L of water. In still more embodiments, the composition is split into two doses. In other embodiments, the composition is split into two doses. In further embodiments, the composition does not cause clinically significant electrolyte shifts in a subject.

In particular embodiments, the composition comprises from about 350.00 grams to about 360.00 grams of polyethylene glycol. In more particular embodiments, the composition comprises from about 15.00 grams to about 20.00 grams of sodium sulfate. In even more particular embodiments, the composition comprises from about 1.60 grams to about 1.90 grams of magnesium sulfate. In yet more particular embodiments, the composition comprises from about 2.00 grams to about 2.40 grams of potassium chloride. In still more embodiments, the composition comprises from about 1.90 grams to about 2.10 grams of sodium chloride. In further embodiments, the composition further comprises from about 1.40 grams to about 1.50 grams of malic acid. In still further embodiments, the composition further comprises from about 1.60 grams to about 1.70 grams of citric acid.

In certain embodiments, the composition further comprises from about 0.40 grams to about 0.45 grams of lemon-lime flavor. In some embodiments, the composition further comprises from about 0.55 grams to about 0.65 grams of sucralose. In some more embodiments, the composition further comprises from about 0.03 grams to about 0.05 grams of neotame. In yet more embodiments, the composition further comprises from about 0.008 grams to about 0.015 grams of advantame. In still more embodiments, the composition further comprises about 2.0 liters of water.

In certain embodiments, the polyethylene glycol is polyethylene glycol 3350.

Aspects disclosed herein also include a method of cleansing the colon. The method comprises administering an effective amount of a composition to a patient, the composition comprising from about 325.00 grams to about 375.00 grams of polyethylene glycol, from about 10.00 grams to about 25.00 grams of sodium sulfate, about 1.00 grams to about 2.50 grams of magnesium sulfate. The effective amount of the composition induces purgation of the colon such that the colon is cleansed.

In certain embodiments, the composition further comprises from about 1.00 grams to about 3.00 grams of potassium chloride and from about 1.00 grams to about 3.00 grams of sodium chloride. In particular embodiments, the method further comprises administering at least 483 ml of water after administering the composition. In more particular embodiments, the composition further comprises water. In yet more particular embodiments, the volume of water is 2.0 liters.

In certain embodiments, the composition is divided into two equal doses prior to administration. In particular embodiments, the two equal doses are administered at least two hours apart. In more particular embodiments, the two equal doses are administered at least four hours apart. In even more particular embodiments, the two equal doses are administered at least six hours apart. In yet more particular embodiments, the two equal doses are administered up to 12 hours apart. In still more particular embodiments, the two equal doses are administered on the same day. In particular embodiments, the two equal doses are administered on separate days. In more particular embodiments, a first of the two equal doses is administered the evening before a diagnostic procedure and a second of the two equal doses is administered on the day of a diagnostic procedure.

In certain embodiments, the composition does not cause clinically significant electrolyte shifts. In some embodiments, the composition further comprises a flavoring agent. In other embodiments, the flavoring agent comprises a flavor and a combination of sweeteners. In further embodiments, the combination of sweeteners comprises sucralose, neotame, and advantame. In still further embodiments, the composition comprises from about 0.400 grams to about 0.500 grams of the flavor. In still other embodiments, the composition comprises from about 0.400 grams to about 0.800 grams of sucralose. In yet further embodiments, the composition comprises from about 0.020 grams to about 0.050 grams of neotame.

In certain embodiments, the composition comprises sodium from about 0.005 grams to about 0.020 grams of advantame. In more certain embodiments, the composition further comprises lemon-lime flavor, sucralose, neotame, advantame, malic acid, and citric acid.

In particular embodiments, the composition comprises about 357.40 grams of polyethylene glycol, about 17.00 grams of sodium sulfate, about 1.800 grams of magnesium sulfate, about 2.240 grams of potassium chloride, about 2.00 grams of sodium chloride, about 0.410 grams of lemon-lime flavor, about 0.600 grams of sucralose, about 0.038 grams of neotame, and about 0.012 grams of advantame. In more particular embodiments, the composition comprises 2.0 liters of water.

Additional aspects disclosed herein include a method of cleansing the colon where the method comprises a) administering an effective amount of a composition to a patient, the composition comprising polyethylene glycol, sodium sulfate, magnesium sulfate, potassium chloride, sodium chloride, and a flavoring agent. The effective amount of the composition induces purgation of the colon such that the colon is cleansed.

In particular embodiments, the composition comprises from about 325.00 grams to about 375.00 grams of polyethylene glycol, from about 10.00 grams to about 25.00 grams of sodium sulfate, about 1.00 grams to about 2.50 grams of magnesium sulfate, from about 1.00 grams to about 3.00 grams of potassium chloride and from about 1.00 grams to about 3.00 grams of sodium chloride.

In certain embodiments, the method further comprises administering at least 483 ml of water after administering the composition. In particular embodiments, the composition further comprises water. In more particular embodiments, the volume of water is 2.0 liters. It should be noted that the salts can be dissolved in a volume of water from about 500 ml to about 2.0 liters. In addition, the composition can be dissolved in about 0.846 liters or about 1.692 liters.

In certain embodiments, the composition is divided into two equal doses prior to administration. In more embodiments, the two equal doses are administered at least two hours apart. In even more embodiments, the two equal doses are administered at least four hours apart. In yet more embodiments, the two equal doses are administered at least six hours apart. In still more embodiments, the two equal doses are administered up to 12 hours apart. In further embodiments, the two equal doses are administered on the same day. In still further embodiments, the two equal doses are administered on separate days.

In certain embodiments, a first of the two equal doses is administered the evening before a diagnostic procedure and a second of the two equal doses is administered on the day of a diagnostic procedure. In more embodiments, the composition does not cause clinically significant electrolyte shifts.

In particular embodiments, the flavoring agent comprises a flavor and a combination of sweeteners. Examples of sweeteners include aspartame, sucralose, acesulfame K, erythritol, saccharin, xylitol, steviol, sorbitol, neotame, advantame, rebaudioside, and lactitol. In more particular embodiments, the combination of sweeteners comprises sucralose, neotame, and advantame. In particular embodiments, the sweeteners comprise non-fermentable carbohydrates. In some embodiments, the composition comprises from about 0.400 grams to about 0.500 grams of the flavor. In other embodiments, the composition comprises from about 0.400 grams to about 0.800 grams of sucralose. In yet other embodiments, the composition comprises from about 0.020 grams to about 0.050 grams of neotame. In still other embodiments, the composition comprises sodium from about 0.005 grams to about 0.020 grams of advantame.

In certain embodiments, the composition comprises about 357.40 grams of polyethylene glycol, about 17.00 grams of sodium sulfate, about 1.800 grams of magnesium sulfate, about 2.240 grams of potassium chloride, about 2.00 grams of sodium chloride, about 0.410 grams of lemon-lime flavor, about 0.600 grams of sucralose, about 0.038 grams of neotame, and about 0.012 grams of advantame.

DETAILED DESCRIPTION

1. Cleansing Compositions

Aspects of the compositions disclosed herein include a dosage composition for cleansing a colon of a subject. The compositions are administered in a liquid composition. As used herein, the term "a" means one or more unless specifically defined otherwise. The disclosed compositions can include a mixture of salts that induce purgation of the colon and are useful to cleanse the colon. When used in appropriate amounts, the disclosed compositions can also relieve constipation, fecal impaction, and the like.

The disclosed compositions obviate the need for patients to mix solutions and also improves cleansing outcomes. Furthermore, the composition allows for a substantial reduction in volume required for a cleansed colon as compared to the MiraLax®/Gatorade® solution, while eliminating the need for bisacodyl as a requirement. Furthermore, another aspect of the disclosed compositions allows for better taste and reduction in gas production caused by fermentation of fermentable sugars. In certain aspects, the compositions utilize non-fermentable sugars.

As disclosed herein, the compositions comprise a mixture of salts. The combination of salts disclosed herein allow for cleansing of the colon in volumes that are tolerable. In addition, the disclosed compositions also can comprise flavoring agents that make commonly unpalatable compositions palatable. Furthermore, the disclosed compositions avoid the issues relating to clinically significant electrolyte shifts. The present inventors have thus created compositions that are safe, tolerable, and effective.

The disclosed compositions, as described herein, can be administered in a single dose or in a split-dose of two or more doses. As used herein, the term "total dose" means the entirety of the amount of active ingredient administered to a patient. In other words, the total dose of the composition is the entirety of the active ingredient administered to the patient whether or not the patient split the total dose into separate doses (i.e., split dose) or took the entire total dose at once. In some embodiments, the total dose can be split into doses administered one the same day or administered on separate days. For instance, the split dose can be administered with one dose on the day before a diagnostic procedure and a second dose on the day of the diagnostic procedure. The two doses are the total dose in this example.

Aspects of the disclosed compositions include a mixture of poorly-absorbable salts. In certain embodiments, the disclosed compositions comprise sulfate salts. Without being held to any particular theory, it is believed that the sulfate anions of the composition are poorly absorbed and remains in the lumen of the intestine. The sulfate anions pull water from the body of the patient into the lumen. The water thus loosens the stool to allow the body to flush the stool from the lumen.

In some embodiments, the disclosed compositions comprise sodium sulfate. In other embodiments, the total dose of composition comprises from about 10.0 grams to about 25.0 grams of sodium sulfate. In specific embodiments, the total dose of composition comprises from about 15.0 grams to about 20.0 grams of sodium sulfate. In more specific embodiments, the total dose of composition comprises about 17.0 grams of sodium sulfate. As used herein, the term "about" means within +/−10% of the recited value. For instance, about 2.0 would cover from 1.8 to 2.2.

In some embodiments, the compositions comprise magnesium sulfate as well as sodium sulfate. As disclosed herein, the compositions comprise sufficient magnesium sulfate (e.g., magnesium sulfate tribasic anhydrous) to induce purgation of the colon.

Magnesium is poorly absorbed by the intestines of a subject and contributes to the osmotic diarrheal action of the composition. When the compositions are administered to subjects with the amounts of magnesium sulfate and sodium sulfate disclosed herein, the compositions will induce purgation of the colon and when administered in sufficient amounts will lead to cleansing of the colon. For instance, when the composition is administered over a period of up to 24 hours, the subject will have sufficient diarrhea to cleanse the colon of stool. In certain embodiments, the compositions comprise from about 1.5 grams to about 2.0 grams of magnesium sulfate. In particular embodiments, the compositions comprise from about 1.7 grams to about 1.9 grams of magnesium sulfate. In specific embodiments, the compositions comprise about 1.8 grams of magnesium sulfate.

The disclosed compositions can also comprise salts in combination with sulfate salts. For instance, the disclosed compositions can comprise salts selected from the group consisting of sodium salts and potassium salts. In some embodiments, the sodium salt is sodium chloride. Sodium chloride can be present in the composition from about 1.0 gram to about 3.0 grams. In certain embodiments, the composition comprises from about 1.5 grams to about 2.5 grams of sodium chloride. In particular embodiments, the composition comprises about 2.0 grams of sodium chloride.

The compositions can also include potassium chloride as the potassium salt. In some embodiments, the composition comprises from about 1.0 grams to about 4.0 grams of potassium chloride. In other embodiments, the composition comprises from about 1.5 grams to about 3.5 grams of potassium chloride. In still other embodiments, the composition comprises from about 2.0 grams to about 3.0 grams of potassium chloride. In specific embodiments, the composition comprises about 2.24 grams of potassium chloride.

Aspects of the disclosed compositions further comprise an acid. For instance, the disclosed compositions can include organic acids. Organic acids include malic acid, citric acid, lactic acid, acetic acid, formic acid, uric acid and oxalic acid. In certain embodiments, the composition comprises malic acid and citric acid. In some embodiments, the composition comprises from about 1.100 grams to about 2.00 grams of malic acid. In specific embodiments, the composition comprises from about 1.200 grams to about 1.700 grams of malic acid. In more specific embodiments, the composition comprises from about 1.430 grams of malic acid. In certain embodiments, the composition comprises from about 1.00 grams to about 2.00 grams of citric acid. In some embodiments, the composition comprises from about 1.20 grams to about 1.80 grams of citric acid. In particular embodiments, the composition comprises from about 1.50 grams to about 1.70 grams of citric acid. In more particular embodiments, the composition comprises about 1.64 grams of citric acid.

Aspects of the disclosed compositions further comprise organic acids packaged separately from the other components of the disclosed composition. In particular embodiments, the organic acids are packaged as a sachet. In some embodiments, the composition comprises from about 1.100 grams to about 2.00 grams of malic acid packaged separately from the other components of the composition. In specific embodiments, the composition comprises from about 1.200 grams to about 1.700 grams of malic acid packaged separately from the other components of the composition. In more specific embodiments, the composition comprises from about 1.430 grams of malic acid packaged separately from the other components of the composition. In certain embodiments, the composition comprises from about 1.00 grams to about 2.00 grams of citric acid packaged separately from the other components of the composition. In some embodiments, the composition comprises from about 1.20 grams to about 1.80 grams of citric acid packaged separately from the other components of the composition. In particular embodiments, the composition comprises from about 1.50 grams to about 1.70 grams of citric acid packaged separately from the other components of the composition. In more particular embodiments, the composition comprises about 1.64 grams of citric acid packaged separately from the other components of the composition. When packaged separately from the other components of the composition, the organic acids can be supplied as any of a tablet, capsule, powder or liquid which may be packaged in one or more of a sachet, blister, bottle or any other pharmaceutically acceptable packaging.

Aspects of the compositions disclosed herein comprise flavoring agents. As discussed herein, prior art compositions suffer from substantial compliance issues. The prior art compositions are mixtures of highly unpalatable salts. The solution to such issues is to attempt to mask the salts with a flavoring agent such as a flavor in combination with one or more sweeteners. Unfortunately, patients still complain of flavors that can render the administration of the solution nauseating or even impossible to complete.

The inventors discovered that a flavoring agent (e.g., a flavor in combination with one or more sweeteners) can lead to a much more palatable and therefore tolerable product. The flavoring agent includes a flavor and one or more sweeteners/sugar substitutes. In some embodiments, the sweeteners are balanced to provide an effective elimination of the salt tastes. In other words, the combination of sweeteners can almost completely eliminate the flavor of the salts in the composition to yield a more pleasing flavor.

Examples of sweeteners useful in the disclosed compositions include aspartame, sucralose, acesulfame K, erythritol, saccharin, xylitol, steviol, sorbitol, neotame, advantame, rebaudioside, and lactitol. In particular embodiments, the sweeteners are non-fermentable carbohydrates. In yet more embodiments, the combination of sweeteners comprises less than about 10%, 5%, 1%, or 0.5% fermentable carbohydrates. In some embodiments, the composition comprises less than about 0.01% fermentable carbohydrates. In yet more embodiments, the combination of sweeteners comprises sucralose, neotame, and advantame. In particular embodiments, the composition comprises about 0.003% of advantame. In certain embodiments, the composition comprises a combination of sucralose and one or both of neotame and advantame. In some embodiments, the composition comprises a combination of sucralose, neotame, and advantame. In particular embodiments, the composition comprises a combination of sucralose, neotame, and advantame in such amounts to eliminate or reduce the flavor of the salts in the compositions.

In other embodiments, the composition comprises from about 0.40 grams to about 0.80 grams of sucralose, 0.020 grams to about 0.060 grams of neotame, and from about 0.005 grams to about 0.020 grams of advantame. In particular embodiments, the composition comprises about 0.600 grams of sucralose, about 0.038 grams of neotame, and about 0.012 grams of advantame. One of ordinary skill in the art will recognize that this combination of artificial sweeteners can be mimicked using other sweeteners.

The combination of sweeteners can also be combined with a flavor. The flavor can be a powder or liquid. In some embodiments, the flavor is a powder. The flavor can be selected from the combination of lemon, lime, lemon-lime, grape, orange, strawberry, or other flavors known in the art. The flavor can be chosen in view of the sweetener combination being used. In some embodiments, the flavor is lemon-lime powder. The lemon-lime powder can be used in an amount from about 0.30 grams to about 0.55 grams of powder in the composition. In certain embodiments, the composition comprises about 0.41 grams of lemon-lime powder (see International Flavors and Fragrances Inc.).

As used in certain aspects disclosed herein, sodium sulfate allows for purging of the colon of a patient to achieve cleansing. In particular uses, sufficient sodium sulfate to participate in cleansing the colon is administered over a period of time (e.g., six or more hours, 12 or more hours, and up to 24 hours). Without being held to any particular theory, the sulfate salts are poorly absorbable and cause water to flow into the intestine when provided in the intestine in sufficient quantities. Poorly-absorbable salts exhibit limited uptake from the intestine and that the salts remaining in the intestine cause water to flow into the intestines. Accordingly, the compositions disclosed herein can be administered with water to induce purgation of the colon of a subject (e.g., patient) and such compositions can be used to cleanse the colon when administered in sufficient quantities. A further advantage of the presently disclosed compositions is that such compositions do not cause clinically significant electrolyte shifts when administered in sufficient quantities to induce purgation of the colon and balanced with other salts as disclosed herein. In some embodiments, the electrolyte shifts that the disclosed compositions avoid are shifts in sodium, magnesium, potassium, and chloride. The disclosed compositions avoid such shifts by providing sufficient amounts of sodium, magnesium, and potassium cations to avoid shifting the levels of these cations in a subject taking the compositions.

Aspects of the disclosed compositions also include polyethylene glycol (also referred to as "PEG"). The disclosed compositions therefore can comprise a combination of sulfate salts, sodium and potassium salts, organic acids, sweeteners, flavorings, and PEG. In certain embodiments, the composition comprises from about 325.0 grams to about 400.0 grams of PEG. In other embodiments, the composition comprises from about 330.0 grams to about 375.0 grams of PEG. In still other embodiments, the composition comprises from about 350.0 grams to about 360.0 grams of PEG. In specific embodiments, the composition comprises about 357.4 grams of PEG. In particular embodiments, the PEG is PEG-3350.

It should be noted that the amounts disclosed herein refer to the total dose administered to a patient. Therefore, the disclosed compositions are the total dose necessary to cleanse the colon unless otherwise stated. Notwithstanding this, the total can be administered in two or more administrations as individual sub-doses. In certain embodiments, the total dose is administered in two sub-doses to a patient over a period of at least six hours, at least eight hours, at least ten hours, at least twelve, or up to 24 hours. The total dose can also be administered in three or more doses over a period of at least six hours, at least eight hours, at least ten hours, at least twelve, or up to 24 hours.

As noted herein, the disclosed compositions are combinations of sodium sulfate, magnesium sulfate, and potassium chloride. The combination of salts and amounts of each salt have been developed to avoid the clinically significant electrolyte shifts found with the use of other solid and hypertonic compositions. This balance of salts allows for inducing of osmotic diarrhea (i.e., purgation) while reducing the clinically significant gains or losses of electrolytes (i.e., shifts of electrolytes) during the process of purgation.

2. Purgative Compositions

In particular embodiments, the compositions are administered in an amount sufficient to induce purgation, the "purgative dose." In particular embodiments, the purgative composition comprises an effective amount of sodium sulfate, magnesium sulfate, sodium chloride, and potassium chloride to induce purgation of the colon. The effective amount of sodium sulfate in combination with magnesium sulfate should be sufficient to induce purgation of the colon. The avoidance of clinically significant electrolyte shifts can be accomplished by the proper balance of potassium chloride, magnesium sulfate, and sodium sulfate. Such balancing of cations to avoid clinically significant electrolyte shifts has been disclosed in U.S. Pat. No. 6,946,149, the contents of which are incorporated herein by reference.

In certain embodiments, the purgative dose of the solution is from about 30% to about 70% of the total dose disclosed herein as effective to cleanse the colon. In some embodiments, the purgative dose of the solution is about 50% of the total dose disclosed herein as effective to cleanse the colon. One of ordinary skill in the art would understand, based on this disclosure, the dose to administer to induce a purgation without cleansing the colon.

3. Methods of Administering Compositions

Disclosed herein are methods of administering the disclosed compositions. Aspects of the disclosed methods comprise administering to the subject an aqueous composition. The aqueous compositions can comprise PEG, mixtures of salts, such as sulfate salts (e.g., sodium sulfate and magnesium sulfate), sodium salts (e.g., sodium sulfate), potassium salts (e.g., potassium sulfate), organic acids (e.g., malic acid and citric acid), combination of sweeteners (e.g., advantame, neotame, and sucralose), and a flavor. The disclosed methods involve administering the disclosed compositions to induce purgation. In some embodiments, the compositions cleanse the colon.

It should be noted that the disclosed methods allow for avoidance of bloating and cramping. In addition, the disclosed methods prevent the degradation of PEG by volatile acids. It was surprisingly discovered that the flavoring agent could be divided and reconstituted prior to administration and still yield a pleasing flavor profile. Indeed, the flavor profile is similar to over-the-counter products such as Gatorade®. This surprising discovery permitted the inventors to utilize PEG, while also utilizing a flavoring agent to mask the extremely unpleasant flavors of PEG and sulfate.

Aspects of the methods disclosed herein include providing a first container of a first portion of a first dose of a colon cleansing product comprising about 170 to about 180 grams of polyethylene glycol, about 5.0 to about 8.0 grams of sodium sulfate, about 0.5 to 3.0 grams of potassium chloride, about 0.4 to about 1.4 grams of sodium chloride, about 0.40 grams to about 0.45 grams of lemon-lime flavor, about 0.55 grams to about 0.65 grams of sucralose, about 0.03 grams to about 0.05 grams of neotame, and about 0.008 grams to about 0.015 grams of advantame.

Aspects further include providing a second container of a second portion of the first dose of a colon cleansing product comprising from about 1.35 grams to about 1.60 grams of malic acid and from about 1.600 grams to about 1.70 grams of citric acid. The method further includes mixing the first container and second container together to form a first mixture and then mixing the first mixture with about 0.5 liters to about 1.0 liters of water to form a first liquid colon cleansing dose. The method further comprises consuming the first liquid colon cleansing dose. The method further comprises providing a third container of a first portion of a second dose of a colon cleansing product comprising about 170 to about 180 grams of polyethylene glycol, about 5.0 to about 8.0 grams of sodium sulfate, about 0.5 to 3.0 grams of potassium chloride, about 0.4 to about 1.4 grams of sodium chloride, about 0.40 grams to about 0.45 grams of lemon-lime flavor, about 0.55 grams to about 0.65 grams of sucralose, about 0.03 grams to about 0.05 grams of neotame, and about 0.008 grams to about 0.015 grams of advantame. Aspects further include providing a fourth container of a second portion of the second dose of a colon cleansing product comprising from about 1.35 grams to about 1.60 grams of malic acid and from about 1.600 grams to about 1.70 grams of citric acid. The method further includes mixing the third container and fourth container together to form a second mixture and then mixing the second mixture with about 0.5 liters to about 1.0 liters of water to form a second liquid colon cleansing dose. The method further comprises consuming the second liquid colon cleansing dose. In some embodiments, the method involves consuming the first liquid colon cleansing dose in 150 ml to 300 ml volumes every 15 minutes. In other embodiments, the method involves consuming the second liquid colon cleansing dose in 150 ml to 300 ml volumes every 15 minutes. In particular embodiments, the method comprises administering the second liquid colon cleansing dose at least 4 hours and no longer than 24 hours after the first liquid colon cleansing dose.

Additionally, the disclosed compositions can be administered with a sufficient quantity of liquid to avoid dehydration caused by the induced purgation. One of ordinary skill in the art would recognize that dehydration is a possible expected event when taking the disclosed compositions with insufficient water. In certain embodiments, the liquid is a clear liquid, such as water. In particular embodiments, the total volume of liquid administered to the subject is from about 500 ml to about 2.0 liters. It should be noted that the salts can be dissolved in a volume of water from about 500 ml to about 2.0 liters. In addition, the composition can be dissolved in about 0.846 liters or about 1.692 liters. The volume of liquid administered to the subject can be adjusted to prevent dehydration (e.g., the volume of liquid can be increased up to 2.0 liters or more depending on the needs of 7.3 grams of sodium sulfate, about 1.12 grams of potassium chloride, about 0.5 grams of sodium chloride, about 0.9 grams of magnesium sulfate, about 0.40 grams to about 0.45 grams of lemon-lime flavor, about 0.55 grams to about 0.65 grams of sucralose, about 0.03 grams to about 0.05 grams of neotame, and about 0.008 grams to about 0.015 grams of advantame. In other embodiments, the fourth container of the second portion of the second dose of a colon cleansing product comprises about 1.35 grams to about 1.60 grams of malic acid and from about 1.600 grams to about 1.70 grams of citric acid.

In yet another embodiment, the composition is split into two or more sub-doses and the sub-doses are administered on the same day. When a split-dose regimen is performed on a single day, each sub-dose of the regimen can be administered with about one hour to about ten hours between administrations of the other sub-dose such that the sub-doses are all administered on the same day.

EXAMPLES

1. Example 1. Composition

Compositions were made and had the following ingredients.

TABLE 1

| Ingredients | BLI4900-2 (2 L) | BLI4900-3 (2 L) | BLI4900-4 (2 L) | BLI4900-5 (2 L) |
|---|---|---|---|---|
| Polyethylene glycol (PEG) 3350 | 300.00 g | 357.40 g | 357.40 g | 357.40 g |
| Sodium Sulfate | 8.880 g | 11.00 g | 17.000 g | 17.000 g |
| Magnesium Sulfate, Anhydrous | 2.400 g | 2.400 g | 1.800 g | 1.800 g |
| Potassium Chloride | 2.240 g | 2.240 g | 2.240 g | 2.240 g |
| Sodium Chloride | | 2.000 g | 0.00 g | 2.00 g |
| Malic Acid | 1.300 g | 1.400 g | 1.436 g | 1.436 g |
| Anhydrous Citric Acid | 1.600 g | 1.600 g | 1.640 g | 1.640 g |
| Flavoring | | | | |
| Lemon-Lime Flavor Powder | 0.600 g | 0.400 g | 0.410 g | 0.410 g |
| Sucralose | 0.700 g | 0.600 g | 0.600 g | 0.600 g |
| Neotame | | | 0.038 g | 0.038 g |
| Advantame | | | 0.012 g | 0.012 g | the particular subject). In particular embodiments, the liquid consumed in two hours or less after ingesting the composition.

In certain embodiments, the first container of the first portion of the first dose of a colon cleansing product comprises about 178.7 grams of polyethylene glycol, about 7.3 grams of sodium sulfate, about 1.12 grams of potassium chloride, about 0.5 grams of sodium chloride, about 0.9 grams of magnesium sulfate, about 0.40 grams to about 0.45 grams of lemon-lime flavor, about 0.55 grams to about 0.65 grams of sucralose, about 0.03 grams to about 0.05 grams of neotame, and about 0.008 grams to about 0.015 grams of advantame. In other embodiments, the second container of the second portion of the first dose of a colon cleansing product comprises about 1.35 grams to about 1.60 grams of malic acid and from about 1.600 grams to about 1.70 grams of citric acid.

In some embodiments, the third container of the first portion of the second dose of a colon cleansing product comprises about 178.7 grams of polyethylene glycol, about Formulation development was achieved through an iterative process following the experimental protocol described below. Each formula was evaluated in a group of 5 or 6 healthy volunteers. The formula composition was then adjusted based on the results to generate the next experimental formula (see Section 3 "Results" below for more further detail).

2. Administration of Compositions i. Study Parameters

Depending on the results from each composition a new composition was designed and evaluated in a subsequent study, etc. Healthy normal male volunteers 18-50 years of age were recruited. Each composition or marketed preparation was studied in groups of five volunteers at a time (one cohort). This was usually repeated to give a total of 10 or more volunteers for each formula.

ii. Study Procedures

Study inclusion criteria required that volunteers were male between the ages of 18 and 50 years; were in good health, as judged by a physical examination and review of medical history; and in the investigator's judgment the subject was mentally competent to sign an instrument of informed consent. All study volunteers signed an approved informed consent document. Exclusion criteria were as follows:

1. Subjects known or suspected of having ileus, gastro-intestinal obstruction, gastric retention, bowel perforation, colitis, megacolon, or colostomy.
2. Subjects with a history of clinically significant abnormal ECGs or a clinically significant abnormal ECG at the screening visit.
3. Subjects on salt-restricted diets, those with a history or evidence of dehydration, ascites, electrolyte disturbances, renal insufficiency, heart disease or who were taking diuretics or other medications that affect electrolytes.
4. Subjects who had a bowel cleansing procedure within the past month or who took a laxative within the past 5 days (120 hours) before dosing.
5. Subjects who had participated in an investigational clinical, surgical, drug, or device study within the past 90 days.
6. Subjects who had hepatitis B or C or were HIV positive at screening.
7. Subjects who were drug users and/or use (have used) alcohol to excess (more than 1 liter of beer per day or the equivalent amount of any other alcoholic beverage).
8. Subjects who had any ongoing medical problems, including diarrhea, or any subject who was scheduled for surgical procedures or who had a history of clinically significant, hepatic, neurologic, hematologic, endocrine, oncologic, pulmonary, immunologic, psychiatric, cardiovascular disease, or any other condition that, in the opinion of the Investigator, would jeopardize the safety of the subject or impact the validity of the study results.
9. Subjects who were allergic to any preparation components; sodium sulfate, potassium sulfate or magnesium sulfate, citric acid or citrate, malic acid, magnesium citrate, magnesium chloride, sodium or potassium bicarbonate, potassium chloride or polyethylene glycol-3350.
10. Subjects who had experienced severe chronic constipation within the past 3 months.

A screening visit was performed within 28 days before confinement in the clinic where, following the informed consent process, study volunteers provided their medical history and vital signs were obtained. Clinical laboratory tests (including serology), a urine drug screen test (including alcohol), a physical examination and 12-lead ECG were performed.

In general, the composition ingestion regimen in these studies employed administration of the composition for a total of two administrations given in a split-dose regimen over two days. Beginning on Day −1, groups of five subjects were confined to the site for up to 48 hours, dependent on the dose schedule. Study volunteers were offered a light meal (breakfast or lunch depending upon the regimen assigned) and were given water (in some experiments clear liquids were allowed) thereafter. Urinalysis, urine drug screen, blood chemistry, hematology and coagulation tests were performed and reviewed to assure the volunteers met study entry criteria. A physical examination was also performed.

iii. Administration of Composition

Beginning at 7 PM, on Day −1, the five study subjects begin taking their composition (Dose 1). The entire administration, together with the 16 ounces of water, was expected to be consumed within approximately 60 minutes. Following completion of the first administration, subjects were instructed to drink two (2) additional servings of 16 ounces of water over the next hour at a rate of approximately 16 ounces of water every fifteen minutes. Blood was collected for clinical chemistry, hematology, coagulation, and sulfate within 60 minutes before Dose 1 administration. Blood samples for clinical chemistry and serum sulfate analysis were also collected at interval after the Dose, usually 4 and 6 hours. In later studies, subjects provided an expiratory air sample prior to administration and at 1, 2, 4, and 6 hours after each Dose to test for hydrogen and methane breath gases. Subjects collected all stool and urine voided beginning at approximately from the time of Dose 1 on Day −1 until prior to Dose 2 (the second administration) on Day 1 (Dose 1 Pool).

Beginning at 7 AM, on Day 1, the subjects begin taking their second administration of composition with 16 ounces of water as before. Following completion of Dose 2, subjects consumed two (2) additional servings of 16 ounces of water over the next hour at a rate of approximately 16 ounces of water each fifteen minutes. As before, blood was collected for clinical chemistry, hematology, coagulation, and sulfate within approximately 60 minutes before Dose 2 and after the Dose, usually at 4 and six hours. In addition, (in later studies) subjects provided expiratory air samples prior to Dose 2 and at 1, 2, 4, and 6 hours following the Dose. Subjects also collected all stool and urine voided beginning at approximately from the time of Dose 2 on Day 1 until check-out (Dose 2 Pool). Subjects remained in the clinic for 8 hours after Dose 2, were offered a standard meal, and released after all procedures were completed.

Each bowel movement (BM) that was passed by a subject after each Dose until prior to the start of the next Dose or the end of study was collected in separate labeled containers, one for each bowel movement. The time and weights of each BM were recorded. Stool solids were measured in the last BM that occurred on or before 4, 6, and 8 hours, and in the final BM sample following each Dose using the method of Patel et al., 2009. After the samples were weighed and aliquots obtained for stool solids, all individual BM samples from each Dose were pooled and analyzed for osmolality and electrolytes (sodium, potassium, chloride, bicarbonate, phosphate, magnesium).

Assessments to determine the efficacy of a given composition included total stool volume (output), percent solids, fecal electrolyte balance, and blood electrolyte results. Beginning with Cohort 7, breath gases were measured as described. Volunteer tolerance to each preparation was monitored and safety was assessed using adverse event data. Descriptive statistics (mean, standard deviation, ranges) were used to compare the data.

3. Results

The intent of these studies was to develop a composition with sufficient stool volume output and percent stool solids (surrogates for cleansing) as well as stool good electrolyte balance (indicating minimal absorption or secretion of electrolytes from the patient during the cleansing process).

Table 2 shows the results of stool output, stool volume, gastric water and electrolyte balance, and blood electrolyte observations.

TABLE 2

|  | BLI4900-2 | BLI4900-3 | BLI4900-4 | BLI4900-5 |
|---|---|---|---|---|
| Subjects | 5 | 8 | 9* | 10 |
| Stool Volume (mL) | 2650.2 (226.8) | 3161.8 (671.9) | 3495.2 (266.5) | 3494.8 (331.6) |
| Scatocrit | 1.71 (1.67) | 1.25 (0.8) | 1.0 (0.3) | 1.5 (1.6) |
| Gastric Water Balance (ml) | 2454.8 (624.8) | 1945.0 (655.0) | 2089.5 (1471.0) | 2114.2 (2046.8) |
| Gastric Electrolyte Balance* Na, K, Cl mEq/L | Na: −53.0 (24.8) K: −4.5 (6.9) Cl: −32.4 (10.8) | Na: −26.3 (56.8) K: −0.4 (7.1) Cl: −20.1 (38.5) | Na: −61.9 (34.9) K: −14.7 (14.2) Cl: −54.9 (20.2) | Na: −13.00 (58.1) K: −12.04 (14.7) Cl: −21.45 (22.5) |
| Blood Electrolytes | Small changes in serum electrolytes. No treatment emergent OOR shifts. | Small changes in serum electrolytes. No treatment emergent OOR shifts. | Small changes in serum electrolytes. No treatment emergent OOR shifts. | Small changes in serum electrolytes. No treatment emergent OOR shifts. |

*Positive values indicate absorption, negative losses.

As shown in Table 2, each of the compositions induced purgation. BLI4900-2, the starting formula, produced low stool volume, therefore it was reformulated to increase stool output by increasing both the PEG and sulfate content. BLI4900-3 produced substantially more stool volume as compared to BLI4900-2, but the cleansing of the composition was less substantial than expected in a separate clinical study which used colonoscopy to assess cleansing efficacy (data not shown), therefore reformulation to further increase stool output was again necessary. This was done by adding additional sodium sulfate. BLI4900-4 had the highest stool volume of the compositions, however, due to the increased diarrheal stool output, it exhibited negative sodium and chloride balance in fecal electrolytes, indicating losses of these electrolytes. Therefore, sodium chloride was added to the formula to increase the amounts of both electrolytes in the solution resulting in BLI4900-5. Testing of BLI4900-5 showed it was associated with nearly identical stool volume to BLI4900-4 and exhibited minimal changes in fecal electrolyte balance. Unlike the prior four formulations, clinical testing of this formulation (4900-5) has indicated acceptable gastrointestinal cleansing (data not shown).

Table 3 below summarizes the adverse events reported for compositions BLI4900-3, BLI4900-4, and BLI4900-5 (the number of subjects reporting the event is in parentheses). As can be seen, the adverse events were generally minor and affected a small number of individuals.

TABLE 3

| Events | | |
|---|---|---|
| BLI4900-3 | BLI4900-4‡ | BLI4900-5‡ |
| Diarrhea* (4) | Hypokalemia (1) | None |
| Nausea (1) | Hyperkalemia (1)** | |
| Headache (1) | Light Headedness (1) | |
| Hypochloremia (1) | Bilateral scleral injection (1) | |
|  | Intermittent excessive salivation (1) | |
|  | Intermittent Rhinitis (1) | |

‡Subjects given formulation 4/5, pending final follow up phone call (30-day diarrhea follow-up)
*Diarrhea defined as "Subjects with 3 or more loose or liquid bowel movements (i.e., a Bristol Stool Rating of 6 or 7) in a 24-hour period will have an adverse event of diarrhea recorded for that day (World Health Organization, 2013)"
**AE was reported 24 hours after Dose 2.

In addition, many patients reported that the formulation was good to excellent regarding flavor and ease of compliance.

What is claimed:

1. A colon cleansing product comprising:

(a) a first container comprising a first portion of a first dose of a colon cleansing product comprising about 178.7 grams of polyethylene glycol 3350, about 7.3 grams of sodium sulfate, about 1.12 grams of potassium chloride, about 0.9 grams of magnesium sulfate, 0.5 grams of sodium chloride;

(b) a second container comprising a second portion of the first dose of a colon cleansing product comprising malic acid and citric acid;

(c) a third container comprising a first portion of a second dose of the colon cleansing product comprising about 178.7 grams of polyethylene glycol 3350, about 7.3 grams of sodium sulfate, about 1.12 grams of potassium chloride, about 0.9 grams of magnesium sulfate, about 0.5 grams of sodium chloride; and (d) a fourth container comprising a second portion of the second dose of the colon cleansing product comprising malic acid and citric acid, wherein the colon cleansing product is formulated so that the combination of the first dose and second dose cleanse a colon of a subject without causing a sodium balance of −50.00 mEq/L or greater in the subject.

2. The colon cleansing product of claim 1, wherein the second portion of the first dose of the colon cleansing product comprises about 1.43 grams of malic acid and about 1.64 grams of citric acid.

3. The colon cleansing product of claim 2, wherein the second portion of the second dose of the colon cleansing product comprises about 1.43 grams of malic acid and about 1.64 grams of citric acid.

\* \* \* \* \*